United States Patent [19]

Haddad

[11] Patent Number: 4,952,514
[45] Date of Patent: Aug. 28, 1990

[54] ANALYSIS OF GOLD, PLATINUM OR PALLADIUM

[75] Inventor: Paul R. Haddad, Eastwood, Australia

[73] Assignee: Uniresearch Limited, New South Wales, Australia

[21] Appl. No.: 172,797

[22] Filed: Mar. 28, 1988

[51] Int. Cl.$^5$ ............ G01N 33/20; B01D 15/08
[52] U.S. Cl. .................... 436/80; 436/84; 436/161; 436/177; 210/198.2; 210/635; 210/656
[58] Field of Search ............ 436/80, 84, 177, 161; 210/198.2, 635, 656

[56] References Cited

U.S. PATENT DOCUMENTS 4,780,113 10/1988 Koslow .................. 210/656

OTHER PUBLICATIONS

Hilton et al., J. of Chromatograph, 361 (1986), pp. 141–150.

Primary Examiner—Robert J. Warden
Assistant Examiner—Lyle Alfandary Alexander
Attorney, Agent, or Firm—Nixon & Vanderhye

[57] ABSTRACT

A method for the analysis of a metal selected from gold, palladium and platinum, when present in solution as cyanide complex, using ion-interaction reverse phase liquid chomatography comprising concentrating the metal cyanide complex on a reverse phase concentrator column, washing the concentrator column to reduce the concentration of interfering species, stripping the metal cyanide complex onto an analytical reverse phase column, eluting the metal cyanide complex from the column, detecting and determining the concentration of the metal in solution by reference to suitable standards. This method has particular utility in the analysis of gold, platinum and palladium bearing cyanide solutions that arise in the carbon-in-pulp method of gold recovery. An apparatus which permits the rapid, accurate analysis of samples using this method is also disclosed.

10 Claims, 4 Drawing Sheets

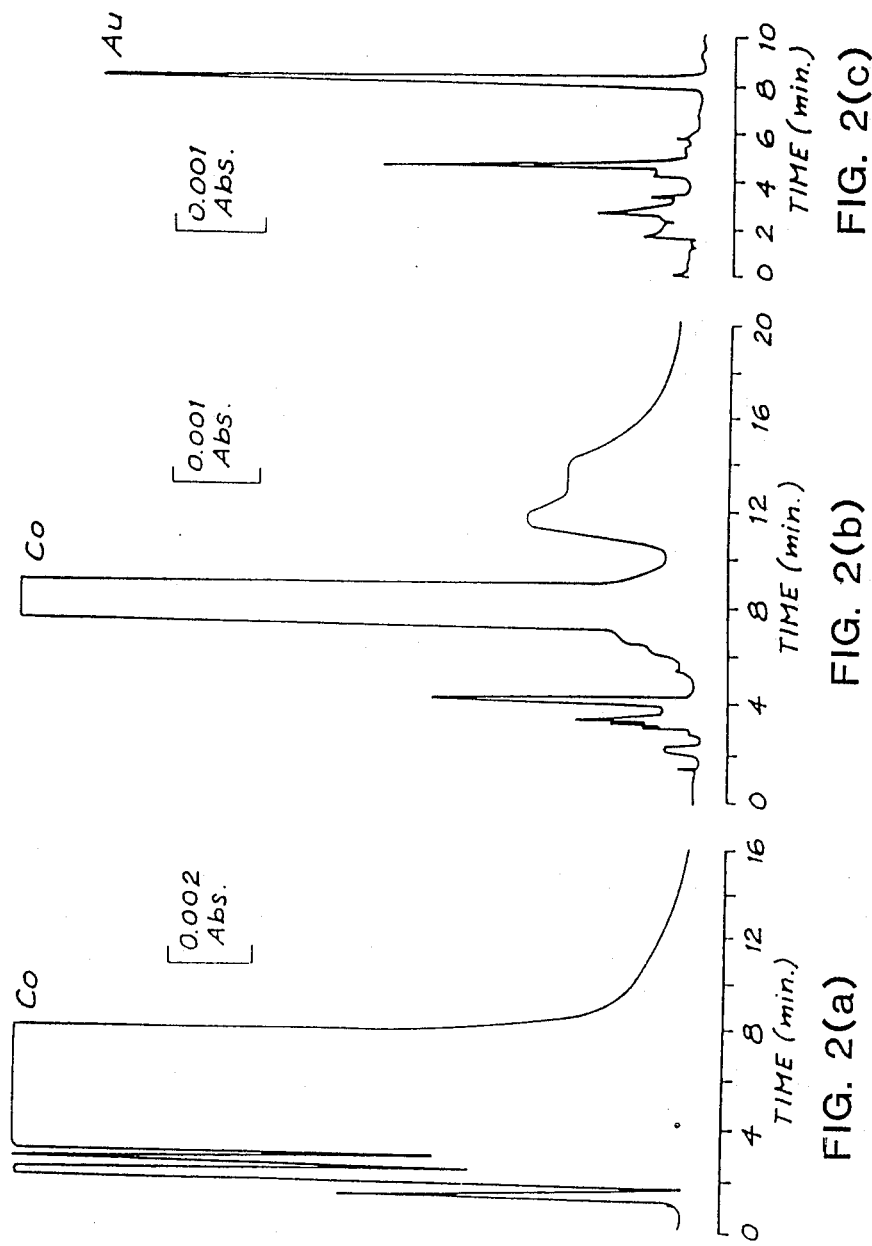

ANALYSIS OF GOLD, PLATINUM OR PALLADIUM

BACKGROUND OF THE INVENTION

This invention relates to apparatus and methods for the analysis of gold and related metals, in particular to an apparatus and method using an ion-interaction reverse phase liquid chomatographic (RPLC) method and apparatus that includes the use of a concentrator column as a means of increasing the limits of detection of the gold and related metals, whilst effectively eliminating matrix interferences.

The art is replete with a variety of methods for the analysis of gold, particularly in ores and process streams. The major methods used are spectroscopic and electrochemical, with atomic absorption spectroscopy using either the flame technique for the determination of gold in ppm concentrations or the carbon furnace for much lower concentrations being the most common method. However, even when using carbon furnace atomic absorption spectroscopy, it is usual to preconcentrate a sample using solvent extraction.

The use of cyanide in the recovery of gold from its ores is by far the most widely used method of gold extraction. One advantage in the use of cyanide is that it frequently permits low grade ores to be effectively treated.

In the cyanide process, an ore is agitated with excess cyanide in the presence of oxygen. Typically, 0.02 –0.08 percent cyanide is reacted with the ore for up to 72 hours with lime being added to neutralise acidic ore components and maintain an alkaline pH. In this reaction, gold is solubilised as gold (I) cyanide whilst other metals that are commonly present are also oxidised and solubilised as a variety of cyano complexes. It is usual that these other metal cyano complexes are present in solution at concentrations much greater than the gold.

One commonly used method for the recovery of gold from these cyanide solutions is the carbon-in-pulp (CIP) process. In this process, the leachate containing aurocyanide in preference to other gold cyano complexes, is passed in a counter-current direction to tanks containing activated carbon, emerging as barren leachate containing only low levels of gold of the order of 10 ppb, that is, 10 parts per $10^9$ parts. The barren leachate is treated to become tailings, whilst the loaded carbon is firstly washed to remove contaminant metal cyano complexes and then aurocyanide is stripped using relatively concentrated alkaline cyanide solutions. Gold may then be recovered electrolytically therefrom, the carbon being reactivated and returned to the process.

To assess the performance of the CIP process, the concentration of gold present at various stages of the process may be monitored. Generally, the concentration of gold will vary from low ppm in the cyanide leachate to low ppb in the barren leachate and tailings. It is to be noted that the most important indicator of process efficiency is obtained from the analysis of these latter solutions.

The present inventor has previously shown that it is possible to analyse cyanide leachate for gold at low ppm levels using ion-interaction RPLC. This method is described in J. Chomatography 361 141 (1986). The essence of this method is the use of a reverse phase $C_{18}$ column and as eluent, acetonitrile-water in the range 23:77 to 30:70, v/v containing 5 mM low UV PIC A.

It was found that this method had three inherent advantages. Firstly, it was specific for aurocyanide which is the most important form of gold for recovery using the CIP process, secondly by optimizing this method, the present inventor found that 40 ppb (0.04 ppm) was the limit of detection and thirdly, other metal cyanide complexes, platinum, palladium and silver could be determined.

However, this method was not suitable for the monitoring of the barren leachate or tailings due to an insufficiently low limit of detection.

Because of the importance of the gold levels in the barren leachate and tailings in the monitoring of the efficiency of a CIP process, the present inventor has recognised that there exists a need for a gold and related metal analytical method that is capable of determining gold when present at sub ppb levels.

SUMMARY OF THE INVENTION

The present inventor has surprisingly found that by preconcentrating a sample of a solution containing gold, platinum and palladium as cyanide complexes on a reverse phase concentrator column, followed by a washing of the column in the same direction as the solution was loaded and then stripping in the opposite direction, using a relatively weak eluent which includes a moderately hydrophobic ion-interaction reagent, gold, platinum and palladium in the resultant strip solution may be determined using a reverse phase analytical column and an appropriate detector. The inventive method permits the assay of gold when present as Au (I) cyanide, palladium as Pd (II) cyanide and platinum as Pt (II) cyanide, with a limit of detection in the case of gold of 0.43 ppb (4.3 parts per $10^{10}$ parts).

In preferred embodiments, use of a stronger eluent on the analytical column permits a marked decrease in analysis time.

In another aspect, the present inventor has found that a novel arrangement of known chomatographic apparatus permits the automated analysis of a sample.

In preferred embodiments of the inventive apparatus, on-line apparatus for the determination of gold in CIP process streams is provided.

DETAILED DESCRIPTION OF THE INVENTION

Accordingly, in one aspect, the present invention consists in a method for the analysis of at least one of gold, platinum and palladium when present in a sample solution as gold (I) cyanide, palladium (II) cyanide and platinum (II) cyanide, comprising the steps of:

(a) conditioning a concentrator column containing a reverse phase material with a weak eluent which includes a moderately hydrophobic ion-interaction reagent;

(b) loading the sample onto the concentrator column;

(c) washing the concentrator column by flowing said eluent through said column in a direction the same as that used for loading the sample;

(d) stripping the at least one of gold (I) cyanide, palladium (II) cyanide and platinum (II) cyanide from the concentrator column and onto an analytical column containing a reverse phase material by flowing said eluent through the concentrator column in a direction opposite to that used for loading said sample;

(e) detecting said at least gold (I) cyanide, palladium (II) cyanide and platinum (II) cyanide, by eluting said analytical column with said eluent; and (f) determining the concentration of at least one of gold, platinum and palladium by comparing the response detected with that obtained from a standard solution of at least one of gold (I) cyanide, palladium (II) cyanide and platinum (II) cyanide.

In another aspect, the present invention further consists in an apparatus for use in the analysis of at least one of gold, palladium and platinum, when present in a solution as gold (I) cyanide, palladium (II) cyanide and platinum (II) cyanide comprising a first valve means adapted to permit the flow of either of two eluents through a connecting means to a second valve means adapted to permit either the flow of a sample solution of said eluents through a connecting means to an inlet of a third valve having two outlets, either of which is adapted to be connected to said inlet, a first of the two outlets, when connected to a said inlet, permitting said sample or said eluents to flow through a connecting means to a first inlet of a fourth valve means and a second of the two outlets, when connected to said inlet, permitting said first or second eluent to flow through a connecting means to a second inlet of said fourth valve means, which valve means has four outlets, said second inlet being adapted to connect to either a third inlet to which there is connected one end of a concentrator column containing a first reverse phase material, or a first outlet of said fourth valve means to which there is connected one end of an analytical column containing a second reverse phase material, said first inlet being adapted to connect to either the other end of a fourth inlet to which there is connected the other end of the concentrator column or a second outlet of said fourth valve means, which outlet permits sample or eluents to flow to waste, a detector connected to the other end of the analytical column, said detector being capable of detecting the presence of at least one of gold (I) cyanide, palladinum (II) cyanide or platinum (II) cyanide and a pump adapted to pump solution or eluent through said valve means, connecting means, concentrator column, analytical column and detector.

Suitably, the reverse phase material may be $C_{18}$ material or neutral styrenedivinylbenzene polymer. Desirably, both columns will contain the same reverse phase material. Preferably, both will be $C_{18}$ columns, the concentrator column being a $C_{18}$ pre-column. For each reverse phase material selected, the composition of the eluent will be varied to obtain optimum results.

A variety of commercially available liquid chromatographs may be used in the analytical method of the invention. A person skilled in the art would readily recognise those instruments suitable for this purpose.

Likewise, whilst it may be possible to use alternative detectors, it has been found that a UV detector operated at 214 nm is suitable for this purpose. Naturally, it may be, however, that the use of a variable wavelength detector could identify other wavelengths giving similar or greater sensitivity.

The eluent may comprise acetonitrile-water or methanol-water in a range of ratios in both cases of from 5:95, v/v to 50:50, v/v, together with a moderately hydrophobic ion-interaction reagent.

Preferably the eluent will comprise acetonitrile-water in a ratio of about 20:80, v.v,/ containing a moderately hydrophobic ion-interaction reagent.

It has been found by the present inventor that tetrabutylammonium ions, preferably as tetrabutylammonium phosphate, in a concentration of about 5 mM constitutes a suitable reagent.

In a preferred embodiment, a first relatively weak eluent containing a moderately hydrophobic ion-interaction reagent is used to condition, wash and strip the concentrator column, whilst a second relatively strong eluent containing a moderately hydrophobic ion-interaction reagent is used to elute the analytical column. The use of this step gradient technique results in a shorter retention time and hence more rapid analysis. The second eluent may comprise acetonitrile-water or methanol-water, generally with the concentration of acetonitrile or methanol in greater concentration than in the case of the first eluent, together with a moderately hydrophobic ion-interaction reagent. Preferably, the second eluent will be acetonitrile-water (30:70, v/v) and the reagent, tetrabutylammonium ions in a concentration of 5 mM.

The invention will now be further described with reference to FIG. 1, comprising FIGS. 1(a), 1(b), 1(c), 1(d) and 1(e), which are schematic diagrams showing the arrangement of the inventive apparatus and various modes of operation in the inventive analysis.

Thus, in FIG. 1(a) there is shown the apparatus as set for a first washing step in which a first eluent 10, acetonitrile-water 20:80 v.v/ containing 5 mM tetrabutylammonium phosphate is used to coat the surface of the concentrator column 11 with the ion-interaction reagent. This is achieved through the operation of pneumatically actuated low pressure valves 12, 13, pump 19 and six port high pressure switching valves 14, 15.

The pump 19 is a model 590 programmable pump whilst all of the valves 12, 13, 14, 15 are combined in a single Waters automated valve switching unit, both being obtainable from Waters Associates (Milford, Mass., USA). The column 11 is a Waters Associates $C_{18}$ Guard-Pak (5.0×6.0 mm I.D.) housed in a Guard-Pak pre-column module.

Figure 1A:
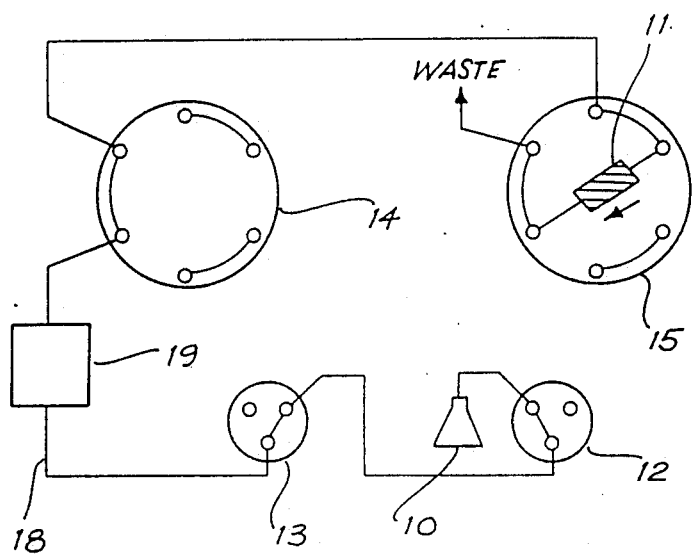
In FIG. 1(b) there is shown the settings for either flushing with sample 16, eluent 10 or second eluent 17. This latter eluent is acetonitrile-water (30:70, v/v) containing 5 mM tetrabutylammonium phosphate. In the step following that shown in FIG. 1a, the sample is used to flush the tubing 18.
In FIG. 1(c), sample 16 is loaded onto the column 11. After this step, the tubing 18 is flushed with eluent 10 as shown in FIG. 1(b).

The column 11 is then washed with eluent 10 as shown in FIG. 1(a). This serves to remove interfering cyano-complexes from column 11.

Figure 1B:
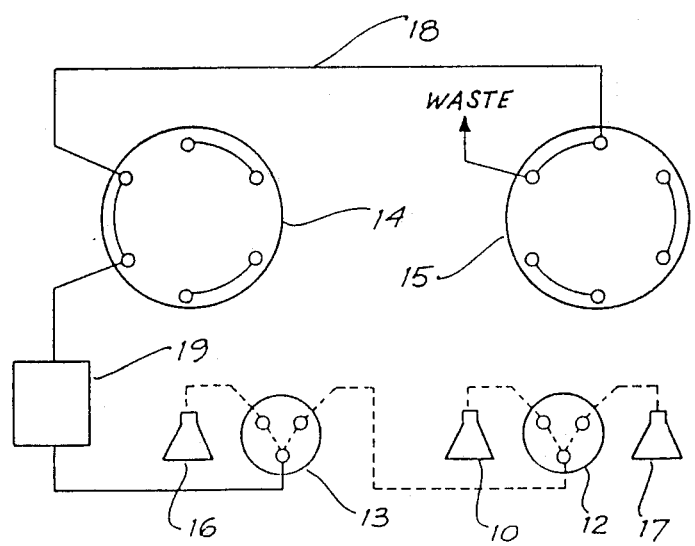
Figure 1C:
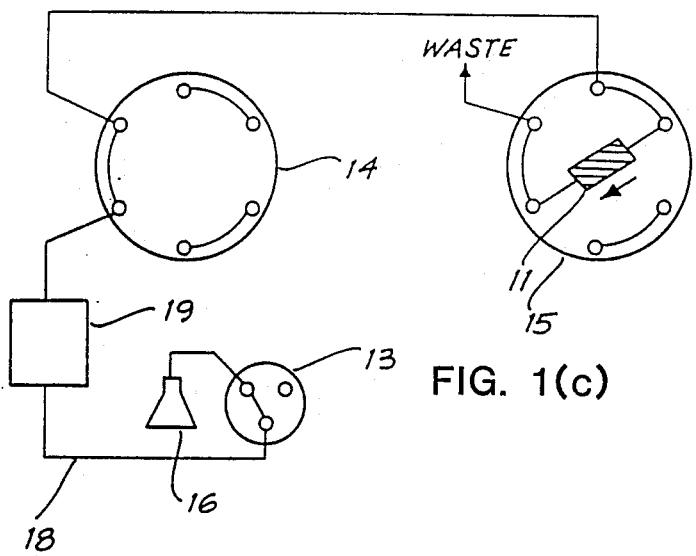
Figure 1D:
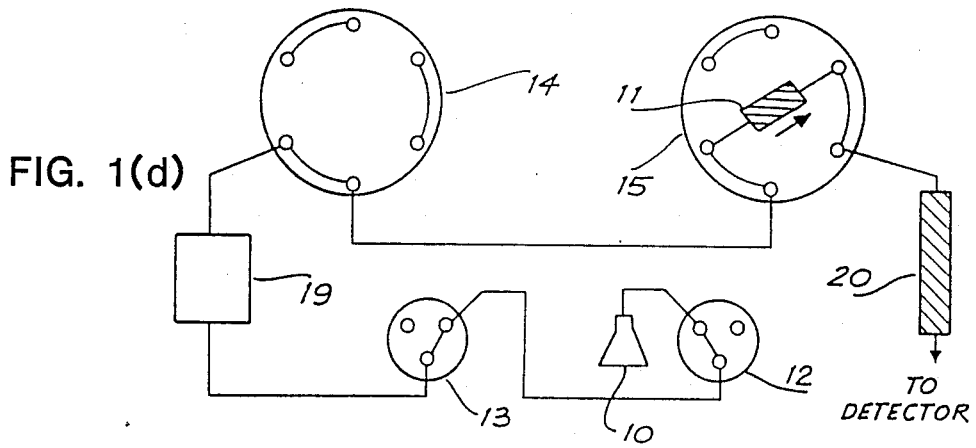

In FIG. 1(d) aurocyanide is stripped from column 11 and transferred onto an analytical column 20, which is a Waters Associates NOVA PAK $C_{18}$ column (150×3.9 mm I.D.). Note that the direction of flow of eluent through column 11 is opposite to that shown in FIG. 1(c).

Figure 1E:
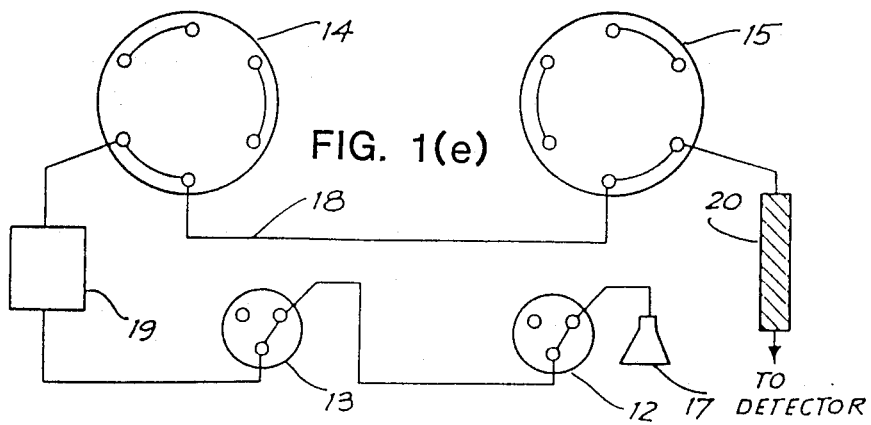

Eluent 17 is then used to flush tubing 18 as is shown in FIG. 1(b). Thereafter, in FIG. 1(e), eluent 17 is used to elute aurocyanide from column 20 and into a detector. The detector is a Waters Associates model 441 UV absorbance detector operated at 214 nm.

The apparatus described in FIG. 1 may be used to analyse CIP tailing solutions. In Table 1, there is shown a basic programme for the analysis of such solutions. The ion-interaction reagent is a low UV PIC A obtained from Waters Associates.

TABLE 1
ANALYSIS OF A TAILINGS SOLUTION

| Step | Mode | Solution delivered | Flow-rate (ml/min) | Volume (ml) | Function |
|---|---|---|---|---|---|
| 1 | Wash | 1st Eluent | 1.0 | 10.0 | Coat the surface of the precolumn with ion-interaction reagent |
| 2 | Flush | Sample | 5.0 | 15.0 | Flush tubing with sample |
| 3 | Load | Sample | 1.0 | 2.0 | Load sample onto precolumn |
| 4 | Flush | 1st Eluent | 5.0 | 15.0 | Flush tubing with 1st eluent |
| 5 | Wash | 1st Eluent | 0.4 | 0.8 | Remove interfering cyano complexes from precolumn |
| 6 | Strip | 1st Eluent | 0.8 | 1.6 | Transfer aurocyanide to analytical column |
| 7 | Flush | 2nd Eluent | 5.0 | 15.0 | Flush tubing with 2nd Eluent |
| 8 | Elute | 2nd Eluent | 1.0 | 15.0 | Elute aurocyanide from analytical column |

1st Eluent = acetonitrile-water (20:80, v/v) containing 5 mM low UV PIC A.
2nd Eluent - acetonitrile-water (30:70, v/v) containing 5 mM low UV PIC A.

Figure 4:
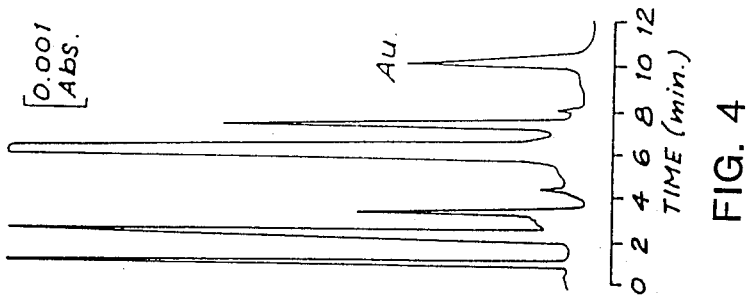

To exemplify the results obtainable using the apparatus and method of the invention, a series of experiments were conducted. The chromatograms that were obtained from these experiments are shown in FIGS. 2, 3 and 4.

In FIG. 2(a) there is shown the chromatogram obtained when 100 micro L of 50 ppm hexacyanocobalt (III) in 100 ppm cyanide is injected directly onto analytical column 20 and eluted with eluent 17 (acetonitrile-water 30:70 v/v). It is evident that the cobalt peak is large.

However, the chromatogram shown in FIG. 2(b) was obtained using 2 mL of the hexacyanocobalt (III) solution when analysed by the inventive apparatus and method with the solution as sample. The cobalt peak is much smaller than that obtained in FIG. 2(a).

Similarly, the chromatogram shown in FIG. 2(c) was obtained using 2 mL of 50 ppb aurocyanide in 100 ppm cyanide.

For the analysis shown in FIGS. 2(b) and 2(c), the wash volume was 200 micro L and the strip volume 600 micro L. Eluent 17 as described above was used as the first and second eluent.

Figure 3C:
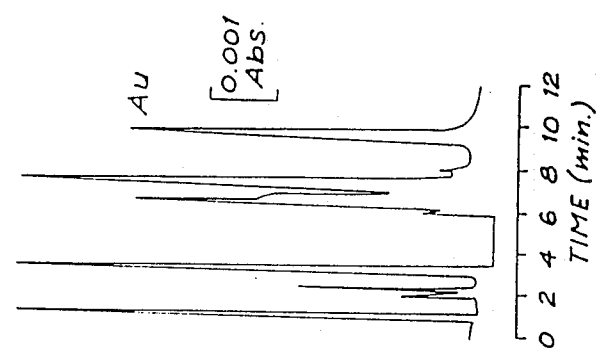
Figure 3B:
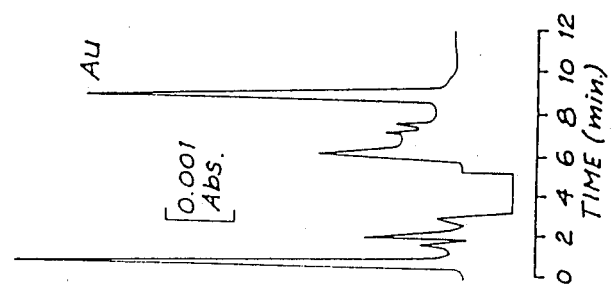
Figure 3A:
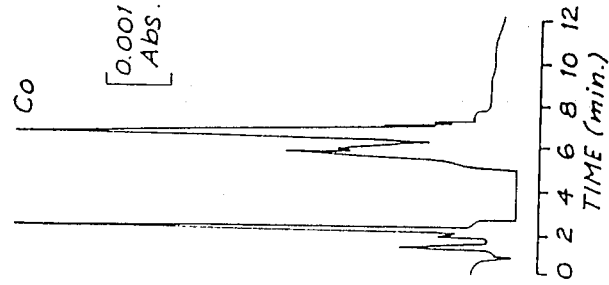

In FIG. 3(a), there is shown the chromatogram obtained for a sample of 2 mL of 5 ppm hexacyanocobalt (III) in 100 ppm cyanide analysed by the inventive apparatus and method, using a first eluent 10 (acetonitrile-water 20:80 v/v) and a second eluent 17 (acetonitrile-water 30:70 v.v/). It is to be noted that the cobalt peak is reduced over that shown in FIG. 2(b).

In FIG. 3(b), the chromatogram obtained for a sample of 2 mL of 50 ppb aurocyanide in 100 ppm cyanide is shown when eluents 10, 17 are used in the inventive apparatus and method. Standard addition experiments and comparison of the aurocyanide peak area to that obtained by direct injection of an identical amount of solute (20 micro L of 5 ppm aurocyanide) showed that the retention of aurocyanide on the concentrator column and its transfer to the analytical column were quantitative.

In FIG. 3(c), the chromatogram obtained for a sample of 2 ml 50 ppb aurocyanide and 5 ppm hexacyanocobalt (III) in 100 ppm cyanide is shown using eluents 10, 17 and the inventive apparatus and method. This clearly shows that the presence of the cyano cobalt complex does not interfere whilst the analysis time for the aurocyanide was less than 10 minutes.

Although the results are not presented herein, the same degree of success was achieved using similar levels of hexacyanoiron (III) and tetracyanonickel (II). Note that in the FIG. 3 experiments, the wash volume was 800 micro L and the strip volume 1600 micro L.

To further illustrate the utility of the inventive apparatus and method, a CIP tailing solution from a gold processing plant was analysed according to the invention. The chromatogram obtained is shown in FIG. 4. For this analysis, the eluent used and other conditions were as described in relation to the FIG. 3 experiment. The example contained 25 ppb gold.

A consideration of the chromatogram shows that the gold was well resolved as a sharp peak which could be readily quantitated. This was achieved in the presence of the elements found in the solution by inductively coupled plasma atomic emission spectroscopy as shown in Table 2.

TABLE 2
ELEMENTAL COMPOSITION OF THE TAILINGS SOLUTION ANALYSED IN FIG. 4.

| Element | Concentration (ppm) |
|---|---|
| Al | 0.4 |
| As | 1.2 |
| C | 87 500 |
| Ca | 480 |
| Co | 1.1 |
| Cu | 12.1 |
| Fe | 6.2 |
| K | 140 |
| Mg | 1420 |
| Mn | 2.4 |
| Na | 15 700 |
| Ni | 1.0 |
| S | 1050 |
| Si | 10.4 |
| V | 3.8 |
| Zn | 0.6 |

Recovery experiments in which the sample was spiked with 10 ppb aurocyanide gave an average recovery of 97.2% for triplicate determinations, thus verifying the quantitative nature of the analysis. The limit of detection was found to be 0.43 ppb gold.

Although the results achieved in the aforementioned experiments were obtained by the optimization of various parameters of the inventive method, it will be appreciated that other gold containing samples may require adjustment of the analytical conditions to achieve comparable results. This may be achieved by a skilled artisan without resort to undue experiment. In particular, the composition of the eluents used may be varied in the ranges taught as well as the volumes of eluents used to wash and strip the concentrator column.

It will also be appreciated that whilst the invention has been described and exemplified in relation to an analysis of aurocyanide, analysis of the corresponding platinum and palladium cyano complexes may be achieved using the inventive apparatus and method.

I claim:

1. A method for the analysis of at least one of gold, platinum and palladium when present in a sample solution as gold (I) cyanide, palladium (II) cyanide and platinum (II) cyanide, comprising the steps of:
   (a) conditioning a concentrator column containing a reverse phase material with a first relatively weak eluent which includes a moderately hydrophobic ion-interaction reagent;
   (b) loading said sample onto the concentrator column;
   (c) washing the concentrator column by flowing said first relatively weak eluent through said column in a direction the same as that used for loading the sample;
   (d) stripping said sample containing at least one of gold (I) cyanide, palladium (II) cyanide and platinum (II) cyanide from the concentrator column and onto an analytical column containing a reverse phase material by flowing said first relatively weak eluent through the concentrator column in a direction opposite to that used for loading said sample;
   (e) detecting said at least gold (I) cyanide, palladium (II) cyanide and platinum (II) cyanide, by eluting said analytical column with a second relatively strong eluent which includes a moderately hydrophobic ion-interaction reagent; and
   (f) determining the concentration of at least one of gold, platinum and palladium by comparing the response detected with that obtained from a standard solution of at least one of gold (I) cyanide, palladium (II) cyanide and platinum (II) cyanide.

2. A method as in claim 1, wherein the sample comprises tailings or barren leachate of a carbon-in-pulp process.

3. A method as in claim 2, wherein said samples also contains at least one of the compounds selected from the group consisting of hexacyanocobalt (III), hexacyanoiron (III) and tetracyanonickel (II) present in a concentration substantially greater than that of the at least one of gold (I) cyanide, palladium (II) cyanide and platinum (II) cyanide.

4. A method as in claim 3, wherein the moderately hydrophobic ion-interaction reagent included in both the first and second eluents is a suitable tetrabutylammonium salt in a concentration of about 5 mM.

5. A method as in claim 4, wherein the same reverse phase material is in both the concentrator and analytical columns and is either a $C_{18}$ material or a neutral styrenedivinylbenzene polymer.

6. A method as in claim 4, wherein the reverse phase material in both the concentrator and analytical columns is a $C_{18}$ material.

7. A method as in claim 6, wherein the first relatively weak eluent is either acetonitrile-water or methonal-water in a ratio of from 5:95 to 50:50, v/v.

8. A method as in claim 7, wherein the first relatively weak eluent is acetonitrile-water, 20:80, v/v.

9. A method as in claim 8, wherein the second relatively strong eluent comprises acetonitrile-water, 30:70, v/v.

10. A method as in claim 9, wherein the response is detected using a UV detector operated at 214 nm.

* * * * *

UNITED STATES PATENT AND TRADEMARK OFFICE
CERTIFICATE OF CORRECTION

PATENT NO. : 4,952,514

DATED : August 28, 1990

INVENTOR(S) : Haddad

It is certified that error appears in the above-identified patent and that said Letters Patent is hereby corrected as shown below:

On the title page, in the left hand column, in item [73] Assignee:, please correct the name of the Assignee to read: --<u>Unisearch</u> Limited--

Signed and Sealed this

Twenty-first Day of April, 1992

Attest:

*Attesting Officer*

HARRY F. MANBECK, JR.

*Commissioner of Patents and Trademarks*